United States Patent [19]

Eby

[11] 4,039,395

[45] Aug. 2, 1977

[54] PURIFICATION OF ACETIC ACID

[75] Inventor: Roy T. Eby, Texas City, Tex.

[73] Assignee: Monsanto Company, St. Louis, Mo.

[21] Appl. No.: 603,825

[22] Filed: Aug. 11, 1975

[51] Int. Cl.$^2$ .......................... C07C 53/08; B01D 3/34
[52] U.S. Cl. .......................................... 203/38; 203/16; 203/66; 203/81; 203/DIG. 19; 260/541
[58] Field of Search .................... 203/16, 63, 66, 38, 203/81, 98; 260/541; 203/99, DIG. 19

[56] References Cited

U.S. PATENT DOCUMENTS

| | | | |
|---|---|---|---|
| 2,433,323 | 12/1947 | Reiter et al. | 203/38 |
| 3,394,058 | 7/1968 | Hohenschutz | 203/16 |
| 3,769,177 | 10/1973 | Eubanks et al. | 203/16 |
| 3,772,156 | 11/1973 | Johnson et al. | 203/38 |
| 3,791,935 | 2/1974 | Eubanks et al. | 203/16 |

*Primary Examiner*—Wilbur L. Bascomb, Jr.
*Attorney, Agent, or Firm*—Elizabeth F. Sporar

[57] ABSTRACT

A process is provided for purification and drying of acetic acid containing water and methyl iodide and hydrogen iodide as contaminants. The process comprises distillation in a two-zone system wherein the major part of the methyl iodide and hydrogen iodide and some water are removed as overhead and bottoms, respectively, from the first zone; a stream from the middle section of the first zone is introduced into a second zone into which there is also introduced a stream of methanol; and a stream of dry purified acid is recovered from the bottom of said second zone. The process provides both for the recovery of the iodine components and the methanol added for re-use in production of additional acetic acid by the reaction of methanol and/or methyl acetate with carbon monoxide in contact with a catalyst system formed on mixing of a rhodium or iridium component and an iodine component in the presence of carbon monoxide.

10 Claims, 1 Drawing Figure

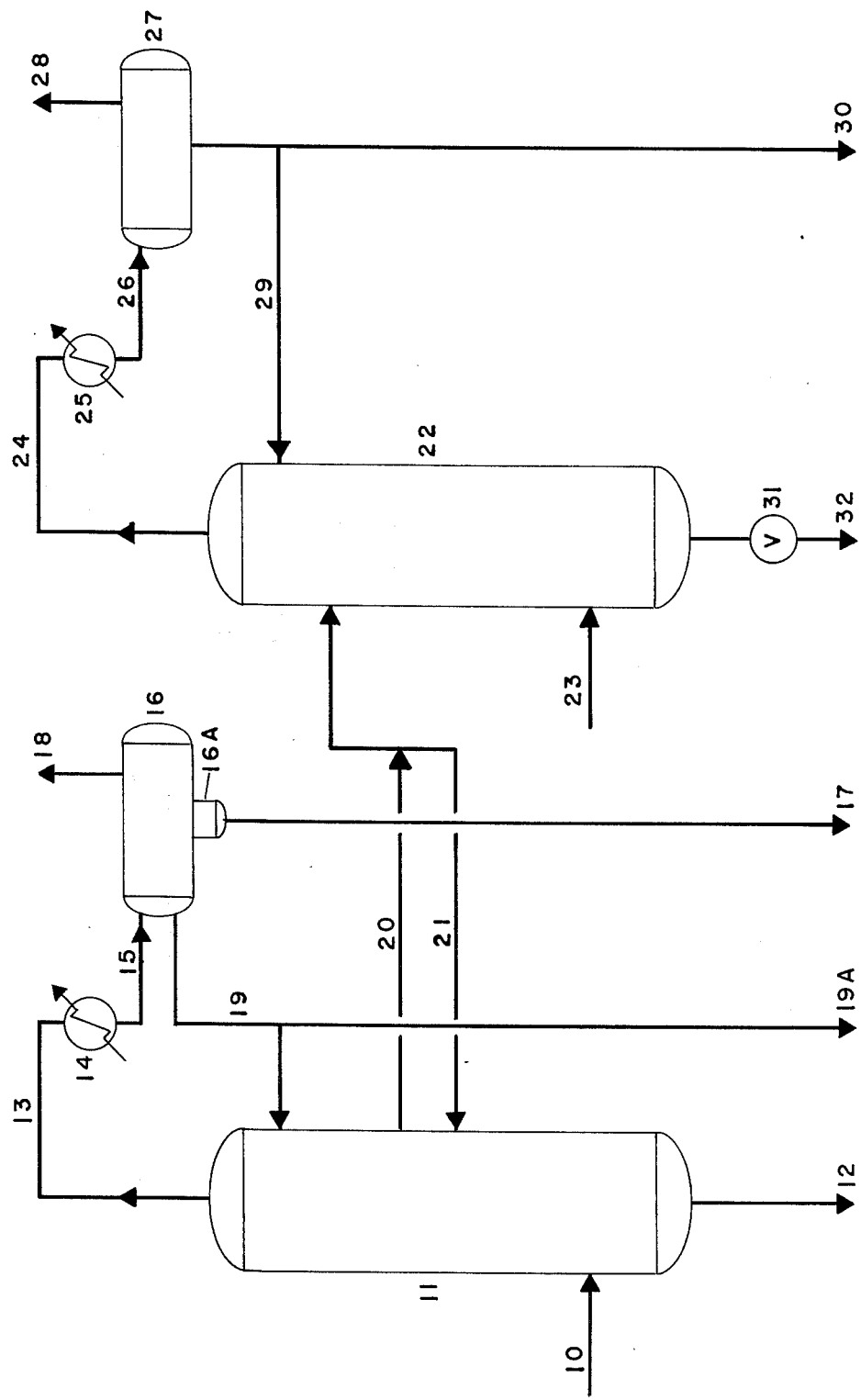

PURIFICATION OF ACETIC ACID

BACKGROUND OF THE INVENTION

The present invention relates to the purification of acetic acid. More particularly, the present invention relates to the purification of product streams of acetic acid produced using a catalytic system containing iodine and which streams contain residual iodine and water.

A process has recently been developed for the preparation of carboxylic acids, notably acetic acid, by the reaction of an alcohol or an ester, or ether and halide derivatives thereof, with carbon monoxide in contact with catalyst systems formed on mixing of a rhodium or iridium component and a halogen component which is usually an iodine component in the presence of carbon monoxide. Hydrogen iodide and/or an alkyl iodide, such as methyl iodide, are employed as the iodine component in these catalyst systems.

While acetic acid produced by the above described process is generally of relatively high purity as far as other organic by-products are concerned, it does contain water and relatively small amounts of iodine as contaminants. In order that the acid can be utilized in further reactions and other uses, it must generally be freed from any water which is present as well as from the small amounts of iodine contaminants present. When freed from such impurities the acid thus produced is admirably suited for practically all uses in commerce and industry of such acid and finds a ready market therein.

A plural-stage distillation system for removal of water as well as the removal of halogen-containing impurities, especially iodine, from streams of carboxylic acids has been described and claimed in U.S. Pat. No. 3,769,177 issued on Oct. 30, 1973. In this process, a stream of carboxylic acid such as acetic acid and containing as contaminants water and certain halogenated materials such as iodine is introduced into a distillation zone. Alkyl halides present such as methyl iodide along with a portion of the water present are removed as an overhead stream from this zone while substantially all hydrogen halides such as hydrogen iodide present are removed in the bottoms stream. A stream from the middle portion of the first distillation zone is removed from said zone and introduced into a second distillation zone wherein there is removed as an overhead stream the remaining portion of the water present. A stream from the middle portion of the second distillation zone is recycled to the first zone and a product acid stream essentially dry and substantially free of the halogen components is removed at or near the bottom of the second distillation zone. This system is generally satisfactory in that there is virtually no waste in the process, all streams being adaptable to recycle to the process for producing the acid mixture which is purified. However, certain disadvantages develop in this system when purifying acetic acid, for example, over long sustained periods of operation. It is difficult to maintain column stability in the second distillation zone. The sidestream taken from this distillation zone is taken from a plate in the middle portion of the zone so selected at a specific temperature and pressure of operation that the concentration of hydrogen iodide is near and, preferably, at the highest of the entire zone on that plate since the purpose of this recycle stream of acid and water is to remove all of the remaining hydrogen iodide present in the second distillation zone. Thus, a special technique is required for control in this zone. Control cannot be effected by the use of conventional distillation control means for monitoring overhead and/or bottoms compositions. In addition, the necessity for withdrawing a sidestream as indicated generally requires a higher temperature than would otherwise be employed which along with the high hydrogen iodide concentration creates an environment conducive to corrosion.

A method has now been discovered for conducting the two-zone distillation for the purification of acetic acid wherein the sidedraw stream from the second distillation zone which is recycled to the first distillation zone can be eliminated to overcome the disadvantages mentioned above. In addition, the new method of operation provides for savings in energy, i.e., stream requirements, and in increased capacity in the system.

SUMMARY OF THE INVENTION

According to the invention, a process is provided for removal and recovery of iodine-containing components and the drying of aqueous acetic acid produced by the reaction of methanol and carbon monoxide in the presence of a catalytic system comprising a rhodium or iridium compound and an iodine-containing component. The process comprises introducing a stream of acetic acid containing as contaminants water, methyl iodide and hydrogen iodide into a first distillation zone intermediate the ends thereof, removing a major proportion of the methyl iodide and a portion of the water overhead from said zone, removing a major proportion of the hydrogen iodide from the bottom of said zone, withdrawing a stream from the middle section of said first distillation zone and introducing said stream into the upper section of a second distillation zone, introducing a stream of methanol into the lower section of said second distillation zone, removing overhead from said second distillation zone the remainder of the water and methyl iodide present together with any methyl acetate generated by the addition of excess methanol into said zone and removing at or near the bottom of said second distillation zone a product acetic acid stream essentially dry and substantially free of hydrogen iodide and methyl iodide.

BRIEF DESCRIPTION OF THE DRAWINGS

The FIGURE is a schematic flow diagram of a specific embodiment of the purification process of the present invention.

DESCRIPTION OF THE PREFERRED EMBODIMENTS

The invention is best understood from the following description thereof with reference to the process flow diagram of the FIGURE. A stream of acetic acid to be purified containing water, methyl iodide and hydrogen iodide in either liquid or vapor form is introduced via line 10 into column 11 intermediate the ends thereof and preferably at a point in the lower half of column 11. The bottoms stream of concentrated acid still containing some water and substantially all of the hydrogen iodide component which has been concentrated in such bottoms is removed via line 12 and preferably recycled to the reactor producing the acid-containing stream. An overhead stream is removed via line 13, condensed in condenser 14, and passed via line 15 to the separator 16. In separator 16, the uncondensed volatile material consisting substantially of carbon monoxide with a minor amount of vaporized methyl iodide can be either vented or returned to the acid-synthesis process via line 18. The liquid present separates into a lighter water phase containing a minor amount of acetic acid and very small quantities of condensed methyl acetate and methyl iodide and a heavier phase containing all the methyl iodide and only small amounts of water, methyl acetate and acetic acid. This heavier phase is concentrated in sump 16A of the separator 16 and is removed via line 17 for return to the acid synthesis step. A portion of the lighter predominantly water phase is recycled via line 19 to column 11 to serve as reflux and the remaining usually minor portion of this lighter phase is recycled via line 19A to the acid-synthesis process.

A stream of principally acetic acid and water is withdrawn from the middle portion of distillation column 11 and passed via line 20 to a second distillation column 22. If required in order to maintain liquid reflux and a minimum water content in column 11 bottoms, provision is made by the junction shown for recycling a portion of the side stream 20 to distillation column 11 via line 21 to below the plate at which the side stream was taken. The side stream 20 entering column 22 is introduced above the mid point of column 22. A stream of methanol is introduced into column 22 via line 23 in the lower part of the column 22. The methanol introduced into the column via line 23 reacts with the hydrogen iodide present and the methyl iodide reaction product is removed overhead from the column via line 24 together with the methyl iodide already in the column, and methyl acetate produced by the addition of excess methanol, and water. The overhead stream is condensed in the condenser 25 and passed via line 26 to separation vessel 27. In this separator 27, any remaining volatile material, generally only carbon monoxide used to maintain the pressure in the column, is either vented or recycled to the acid-synthesis process via line 28. The relatively dilute acetic acid liquid solution present in separator 27 is split as shown to supply a portion as reflux to the distillation column 22 via line 29 with the other portion of said dilute solution being withdrawn via line 30 for either disposal or recycle to the acid-synthesis process.

As a result of treatment and distillation in column 22, a purified acid collects in the bottom of the column and is withdrawn via valve 31 and line 32. Alternatively, the product acetic acid can be withdrawn in vapor form via line 33 from a point above the liquid level near the bottom of the column. Either product acetic acid stream is essentially dry and substantially free of the iodine components present in the original crude acid stream charged to the system via line 10.

It will be apparent from the description that the introduction of methanol into the column effects the removal of hydrogen iodide by chemical means and eliminates the necessity for the sidestream in the prior art process which is recycled to the first distillation column. This reduces steam (energy) requirements since redistillation of the sidestream is no longer required and results in increased through-put in both columns. Stability of operation of the column is also increased since conventional control can be effected by means of the bottoms composition. In addition, there is still virtually no waste from the process of the invention, since all the streams withdrawn are suitable for recycle to the reaction process producing the acid mixture which is purified. Thus, the present process is extremely economical in the recovery of the active iodine components of the catalyst as well as of the methanol added to facilitate such recovery for subsequent re-use in the catalytic production of additional acetic acid.

Acetic acid containing water and at least one iodine-containing contaminant as an impurity is amenable to purification by the present process irrespective of the manner in which it is produced. Generally, however, the acid to be purified is produced by the reaction of methanol and/or methyl acetate and carbon monoxide in the presence of a catalyst system containing a rhodium or iridium component and a halogen component which is iodine or iodine-containing such as methyl iodide and/or hydrogen iodide.

The columns employed in the purification process outlined above can comprise any distillation columns normally used for separation and purification and can be either the packed or plate type or can be a combination packed-plate type. Generally, the first zone will comprise a plate-type column having from 2 to 25 trays and preferably from 5 to 20 trays. Sieve trays are preferably employed although other type trays such as bubble cap and ballast can be used.

The second distillation zone can, as in the case of the first distillation zone, comprise any distillation column normally employed for the separation and purification of fluids. It can also be of the packed or plate type or a combination of the two. Generally, the second distillation zone will comprise a plate-type column having from 10 to 90 trays and preferably from 20 to 60 trays. Although bubble cap trays and ballast trays may be employed in the column comprising the second distillation zone, it is preferred that sieve trays be used.

The associated condensers and liquid separation vessels employed with each of the distillation columns described are of generally conventional design and manufacture. They can be of the open vessel type or can contain baffles or other means for suppressing surging if desired. It is preferred that the liquid phase separation vessel 16 associated with the overhead stream from the first distillation zone have provision for an internal or external sump for collection of the concentrated heavy liquid phase separated therein.

As will be recognized, various pumps, compressors, reboilers, separation vesels, etc., normally employed in carrying out chemical processes can be employed in the process described herein. Since these do not form part of this invention, the details of their use in various phases of the process description have not been included.

The temperatures and pressures employed in the two distillation zones described above may vary. As a practical matter, pressures from 1 to 5.3 kg/cm$^2$ will generally be employed in these zones although subatmospheric pressures may be employed if desired as well as superatmospheric pressures well in excess of 5.3 kg/cm$^2$. Preferably, pressures within the range of 1 to 4.2 kg/cm$^2$ are employed. Temperatures within the zones will normally lie between the boiling point of the acetic acid being purified and approximately the boiling point of water at the pressure of the zone. At the pressures indicated above, the bottoms temperature of the two zones will generally be within the range from approximately the boiling point of acetic acid at the pressure employed to as high as 165° C or higher but preferably below about 165° C. The temperatures at the top of the distillation zones likewise range from the boiling point of the acid at the pressure employed to as low as 100° C. The temperatures and pressures of the two distillation zones may be the same or different but most often the temperatures and pressures of the second distillation zone are maintained at somewhat higher levels than those of the first distillation zone.

Although the point of introduction of the acid to be purified can vary intermediate the ends of the zone, the feed stream to the first distillation zone is usually introduced into the lower half of that zone and preferably into the lower third thereof. While the stream fed to the second distillation zone can be removed from any point in the middle portion of the first distillation zone above the point of introduction of the feed stream thereto and below the point of overhead reflux, it is preferably withdrawn at an intermediate point in this section where the composition present is approximately 80% acid and 20% water at the temperature and pressures prevailing in that zone. This stream can then be introduced anywhere in the upper half of the second distillation zone but preferably is introduced into the upper one-third of the second distillation zone.

The methanol added at line 23 into the second distillation zone is introduced at a point in the lower half of said zone. Preferably, it is introduced into the lower one-fourth of said zone. The amount of methanol introduced will vary depending upon the content of hydrogen iodide in the second distillation zone. On a weight basis, the amount of methanol introduced is from one part per part of hydrogen iodide present to twenty parts per part of hydrogen iodide present, i.e., a methanol-to-hydrogen iodide weight ratio from 1:1 to 20:1 can be used. Preferably, this ratio is maintained in the range from about 2:1 to about 7:1.

The product acid stream removed from the second distillation zone can be removed at any point in the lower one-third and preferably from the lower one-tenth of this zone. If a fully condensed liquid product is desired, the most desirable point for withdrawal of the product stream from this second distillation zone yielding the driest acid product is at the bottom of the zone. Alternatively, if a product stream free of any trace of metallic halide impurities is desired, the product stream should be withdrawn in vapor form from a point above the liquid level of the second zone bottoms. A convenient point is just at or below the lowest plate in the second distillation zone. The purified acetic acid stream thus realized is suitable for most applications, both commercial and otherwise, in which this acid is generally employed. However, if it is desired that the acetic acid product be virtually completely free of any iodine contamination because of the very stringent requirements in specialized uses for the highly purified acid in catalytic systems in which the catalyst is most sensitive to even trace amounts of iodine impurities, then this acid product can be subjected to further even more strenuous purification by additional treatment or processes. Such additional treatment or processes, however, form no part of the present invention.

The percentages of the feed (10) to the first distillation zone which are removed in the various fractions taken from that zone can vary somewhat. Generally the overhead stream removed from the first distillation zone and either recycled to supply reflux thereto (19) or recycled to an earlier stage of the acid synthesis process employed (19A) will range from approximately 65 to 85% and preferably from 70 to 80% by weight of the feed (10) to the first distillation zone. The proportion of the feed (10) to the first distillation column withdrawn from the middle portion of the first zone and introduced into the second distillation column (20) will generally be from about 35 to about 60% and preferably from about 45 to about 55% by weight of said feed to the first distillation zone. The bottoms stream removed from the first distillation zone constitutes from about 1 to about 5 per cent by weight of the feed (10) to that zone and preferably is from about 1 to about 3% of said feed.

As in the case with the first distillation zone, some variation can also occur in the percentages of the total feed to the second distillation zone represented by removal of the different fractions taken from this zone. The amount of the overhead stream removed can be varied since in the case of this stream the portion recycled as reflux to the upper section of the second distillation zone can be adjusted concurrently. This overhead stream generally represents from about 60 to about 70% by weight of the feed (10) including the methanol fed to the second distillation column. Methanol is added to the second distillation zone at a rate of about 0.2% by weight of the feed to the column. The withdrawal rate of the bottoms stream of purified acetic acid product is not limited but care must be taken to retain sufficient liquid bottoms in the second distillation zone to accommodate the heat input from a reboiler or other heating means and to avoid starving this bottom zone to dryness.

The following example is represented to illustrate the process of the present invention and to demonstrate its effectiveness but is not intended to restrict the invention in any manner whatsoever. Unless otherwise stated, all parts and percentages given are by weight.

EXAMPLE

A stream of acetic acid containing water, hydrogen iodide and methyl iodide which had been produced by the reaction of methanol with carbon monoxide in contact with a catalyst system containing a rhodium component and an iodide component was dried and purified of its iodine content in a purification and recovery system like that shown in the FIGURE. The first distillation column contained 14 trays, five valve trays, one total liquid draw-off tray and eight sieve trays, while the second column contained 47 sieve trays. An acid stream containing approximately 0.6% carbon monoxide, 34% methyl iodide, 14% water, 2% methyl acetate, 200 ppm hydrogen iodide and the remainder acetic acid was introduced into the first column between the second and third tray from the bottom at a rate of about 1740 parts per hour. The column was operated at a temperature of about 125° C and a pressure of about 3 kg/cm$^2$. A stream containing about 92% acetic acid, 7% water and 1% hydrogen iodide was withdrawn from the bottom of the first column at a rate of about 18 parts per hour and returned to the acid synthesis process. The overhead vapors from the column were condensed and passed to a separator where the uncondensed carbon monoxide and a minor amount of methyl iodide were vented to the atmosphere. The condensed material separated into two phases, the lighter phase containing about 50.6% water, 36.1% acetic acid, 5.5% methyl acetate, 7.2% methyl iodide and 0.5% methanol, the heavier phase containing 93.7% methyl iodide, 0.2% water, 3.1% acetic acid and 3.1% methyl acetate. About 415 parts per hour of the lighter phase was returned to the column as reflux while the remainder was withdrawn for return to the acid synthesis step. The heavier phase was removed at a rate of about 650 parts per hour and recycled to the acid synthesis process.

A stream consisting of 82.8% acetic acid, 14.1% water, 2.2% methyl iodide, 1% methyl acetate and 2500 ppm of hydrogen iodide was withdrawn from tray 6 of the first column at a rate of about 740 parts per hour and introduced into a second distillation column at tray 30 (numbered from the bottom). A stream of methanol was likewise introduced into this second column of tray 8 at a rate of 12.5 parts per hour where the temperature was about 40° C and the pressure about 4.5 kg/cm². The vapors coming overhead from the second column operating at an overhead temperature of 133° C and pressure of ~4.5 kg/cm² were condensed and passed to a separator. All remaining volatile material, mostly CO, was removed for recycle to the acid synthesis step. The condensate containing about 33.4% acetic acid, 57% water, 5.6% methyl iodide and 4% methyl acetate was split with 270 parts per hour being returned to the column as reflux and 220 parts per hour being with drawn for recycle to the acid synthesis plant.

A product acetic acid stream was removed from the bottom of the second column at a rate of about 530 parts per hour. The acid thus produced was analyzed and found to contain 99.96% acetic acid, 0.03% water and about 100 parts of hydrogen iodide per billion parts of acid (ppb).

What is claimed is:

1. A process for the removal and recovery of iodine-containing components and the drying of acetic acid which consists of
   a. introducing a stream of acetic acid containing water, methyl iodide and hydrogen iodide into a first distillation zone intermediate the ends thereof,
   b. removing as an overhead fraction from said first distillation zone the major proportion of the methyl iodide and a portion of the water,
   c. removing from the bottom of said first distillation zone the major proportion of the hydrogen iodide,
   d. withdrawing a stream from the middle section of said first distillation zone and introducing at least a portion of said stream into the upper section of a second distillation zone,
   e. introducing a stream of methanol into the lower section of said second distillation zone,
   f. removing overhead from said second distillation zone a stream containing the remainder of the water and methyl iodide present together with any methyl acetate generated by the addition of excess methanol into said zone, condensing said stream, returning a portion thereof as reflux to said second distillation zone and removing the remaining portion thereof from said secnd distillation zone, and
   g. removing at or near the bottom of said second distillation zone a product acetic acid essentially dry and substantially free of hydrogen iodide and methyl iodide.

2. The process of claim 1 wherein the stream of step (a) is introduced into the lower third of said first distillation zone.

3. The process of claim 2 wherein the stream of step (d) is introduced into the upper one-third of said second distillation zone.

4. The process of claim 3 wherein the stream of step (e) is introduced into the lower one-fourth of said second distillation zone.

5. The process of claim 4 wherein the amount of methanol introduced is from one part by weight to 20 parts by weight per part by weight of hydrogen iodide contained in said zone.

6. The process of claim 5 wherein the weight ratio of methanol introduced into said second distillation zone to the hydrogen iodide contained in said zone is from about 2:1 to about 7:1.

7. The process of claim 5 wherein the overhead fraction of step (b) is condensed and separated into a light phase and a heavy phase, a portion of said light phase being returned as reflux to the upper part of said first distillation zone.

8. The process of claim 7 wherein a portion of the withdrawn stream of step (d) is recycled to said first distillation zone below the point at which said stream of step (d) is withdrawn from said first distillation zone and wherein the recycle step takes place upstream of the introduction of said withdrawn stream into said second distillation zone.

9. The process of claim 8 wherein the stream of step (g) is removed from the bottom of said second distillation zone.

10. The process of claim 8 wherein the stream of step (g) is removed in vapor form from a point above the liquid level in the bottom of said second distillation zone.

* * * * *